United States Patent
Schaefer et al.

(10) Patent No.: US 10,929,974 B2
(45) Date of Patent: Feb. 23, 2021

(54) DETERMINING CALCIUM CONTENT FROM SPECTRAL CT DATA

(71) Applicant: KONINKLIJKE PHILIPS N.V., Eindhoven (NL)

(72) Inventors: Dirk Schaefer, Hamburg (DE); Heiner Daerr, Hamburg (DE); Thomas Koehler, Norderstedt (DE); Ewald Roessl, Ellerau (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 42 days.

(21) Appl. No.: 16/301,477

(22) PCT Filed: Jun. 14, 2017

(86) PCT No.: PCT/EP2017/064590
§ 371 (c)(1),
(2) Date: Nov. 14, 2018

(87) PCT Pub. No.: WO2017/216248
PCT Pub. Date: Dec. 21, 2017

(65) Prior Publication Data
US 2019/0295249 A1 Sep. 26, 2019

(30) Foreign Application Priority Data
Jun. 15, 2016 (EP) ..................... 16174535

(51) Int. Cl.
*G06K 9/00* (2006.01)
*G06T 7/00* (2017.01)
(Continued)

(52) U.S. Cl.
CPC .......... *G06T 7/0012* (2013.01); *G06T 11/005* (2013.01); *G16H 30/40* (2018.01);
(Continued)

(58) Field of Classification Search
CPC . G06T 2207/10081; G06T 2207/30048; G06T 2207/30101; G06T 2211/404;
(Continued)

(56) References Cited

U.S. PATENT DOCUMENTS

2003/0184730 A1* 10/2003 Price .................. G06T 5/50
356/39
2004/0136491 A1* 7/2004 Iatrou ................ A61B 6/4035
378/4
(Continued)

FOREIGN PATENT DOCUMENTS

| WO | 2015092588 | 6/2015 |
|----|------------|--------|
| WO | 2016038169 | 3/2016 |

OTHER PUBLICATIONS

Guanyu et al, (Automatic coronary calcium scoring using noncontrast and contrast CT images, Med. Phys. 43 (5), May 2016, pp. 2175-2186) (Year: 2016).*
(Continued)

*Primary Examiner* — Amara Abdi
(74) *Attorney, Agent, or Firm* — Larry Liberchuk

(57) ABSTRACT

Present invention relates to devices and methods for determining a calcium content by analyzing cardiac spectral CT data. CT projection data (9), obtainable by scanning a cardiac region of a subject using a spectral CT scanning unit, is modelled (12) by applying a material decomposition algorithm to the projection data to provide a calcium-specific component. Tomographic reconstructions (13) of the projection data, to provide a first 3D image (8), and of the calcium-specific component, to provide a second 3D image (6), are performed. The first 3D image (8) is segmented (14) to provide an image mask (5) corresponding to a cardiovascular structure of interest, a part of the second 3D image (6) is selected (15) based on the image mask (5), and
(Continued)

a calcium content is calculated (16) in the cardiovascular structure of interest based on the selected part of the second 3D image (6).

16 Claims, 2 Drawing Sheets

(51) Int. Cl.
  *G16H 30/40* (2018.01)
  *G06T 11/00* (2006.01)
  *A61B 5/02* (2006.01)

(52) U.S. Cl.
  CPC . *A61B 5/02007* (2013.01); *G06T 2207/10081* (2013.01); *G06T 2207/30048* (2013.01); *G06T 2207/30101* (2013.01); *G06T 2211/404* (2013.01); *G06T 2211/408* (2013.01)

(58) Field of Classification Search
  CPC ............. G06T 2211/408; G06T 7/0012; G06T 11/005; A61B 5/02007; G16H 30/40
  See application file for complete search history.

(56) References Cited

U.S. PATENT DOCUMENTS

| | | |
|---|---|---|
| 2004/0184574 A1 | 9/2004 | Wu |
| 2007/0041490 A1 | 2/2007 | Jha |
| 2008/0159610 A1 | 7/2008 | Haas |
| 2009/0136107 A1* | 5/2009 | Arnold ..................... G06T 7/62 382/131 |
| 2012/0076377 A1 | 3/2012 | Dutta |
| 2014/0050378 A1 | 2/2014 | Sengupta |
| 2017/0161923 A1* | 6/2017 | Nakano ................. G06T 3/4007 |

OTHER PUBLICATIONS

Roessl, et al., "K-edge imaging in x-ray computed tomography using multi-bin photon counting detectors", Physics in Medicine and Biology; vol. 52, No. 15, Aug. 7, 2007.

Arad, et al., "Prediction of coronary events with electron beam computed tomography", Journal of the American College of Cardiology, vol. 36, Issue 4, Oct. 2000, pp. 1253-1260.

Fischbach, et al., "Coronary Calcium Scoring With Multidetector-Row CT", Rationale and Scoring Techniques, Chapter 12, From: Contemporary Cardiology: CT of the Heart, Springer, 2007.

Fuchs, et al., "Coronary artery calcium quantification from contrast enhanced CT using gemstone spectral imaging and material decomposition", Int J Cardiovasc Imaging (2014) 30:1399-1405.

Mendonça, et al., "Multi-Material Decomposition of Spectral CT Images", Medical Imaging 2010: Physics of Medical Imaging.

Song, et al., "Virtual Non-Contrast CT Using Dual-Energy Spectral CT: Feasibility of Coronary Artery Calcium Scoring", Korean J Radiol 2016;17(3):321-329.

* cited by examiner

US 10,929,974 B2

DETERMINING CALCIUM CONTENT FROM SPECTRAL CT DATA

CROSS REFERENCE TO RELATED APPLICATIONS

This application is the U.S. National Phase application under 35 U.S.C. § 371 of International Application No. PCT/EP2017/064590 filed Jun. 14, 2017, published as WO 2017/216248 on Dec. 21, 2017, which claims the benefit of European Patent Application Number 16174535.1 filed Jun. 15, 2016. These applications are hereby incorporated by reference herein.

FIELD OF THE INVENTION

The invention relates to the field of computed tomography (CT) imaging and related image processing. More specifically it relates to a system and a method for analyzing images obtained by computed tomography, and a computer program product for implementing such method.

BACKGROUND OF THE INVENTION

In radiologic cardiovascular examination, determining a calcium content may be particularly useful, e.g. for determining a coronary artery calcium score. Such calcium score is a measurement known in the art for determining, e.g. estimating and/or quantifying, the amount of calcium that is present in the walls of arteries that supply the heart muscle. This amount of calcium is correlated with hardening of the arterial wall, e.g. may indicate an arteriosclerotic vascular disease, such as, particularly, atherosclerosis. In atherosclerosis, a plaque is formed on the arterial wall, which may comprise a nodular accumulation of atheroma, crystal deposits of cholesterol and, particularly, calcification at the outer base of more advanced lesions. When an atherosclerosis condition is allowed to develop further, accumulated material adhering to the walls may release suddenly to form intraluminal thrombi which can occlude a coronary artery supplying the heart muscle, thus causing a myocardial infarction, or which can form a thromboembolism. Atherosclerosis may be chronic, yet asymptomatic for decades.

Therefore, a coronary artery calcium score may represent an important indicative variable for evaluating, in conjunction with other diagnostic variables, patient history and other relevant medical parameters, a risk of a heart attack or stroke in the future, e.g. over a period of a few to about ten years. Since calcium in the coronary arterial walls is a marker of coronary artery disease (CAD), the amount of calcium detected on a cardiac CT scan, and quantified by a calcium score, forms a helpful prognostic tool. Calcium scoring allows for an early risk stratification, since patients with a high score have an increased risk for major adverse cardiac events. Nonetheless, a high calcium score does not imply that an individual will suffer a major adverse cardiac event in the future, e.g. a heart attack, and a low calcium score does not imply that an individual will not suffer such event, e.g. the calcium score is merely a quantifiable parameter indicative of a health-related stochastic. While a calcium score quantifying, e.g. estimating, the amount of coronary calcium may be an important marker of coronary atherosclerosis, it does not necessarily reflect a narrowing of the vessel, e.g. a degree of stenosis.

It is known in the art to estimate the extent of coronary artery calcification by calcium scoring using an unenhanced low-dose computed tomography (CT) scan. Such unenhanced low-dose CT scan may be a dedicated CT scan that is routinely performed, specifically for this purpose, in patients undergoing cardiac CT. While reference may be made, generally, to patients in the present description, it will be understood by the skilled person that a CT image for calcium scoring, e.g. a volumetric image, may be obtained by performing a CT scan that constitutes, or forms part of, a screening examination. Thus, while reference can be made in the present description to a "patient", it will be understood that such patient does not necessarily present any signs or symptoms of an illness, but may equally refer to a healthy person for which information is gathered in order to determine whether a medical illness might be present or whether a substantial probability of developing a serious illness exists.

It is known in the art to perform CT imaging for calcium scoring in breath-hold with ECG triggering or retrospective gating, in which a volumetric image may be acquired by multiple axial scans or a helical scan. Furthermore, residual breathing or cardiac motion may deteriorate the calcium scores derived from such volumetric images acquired by a known technique, e.g. due to image blurring.

The attenuation, e.g. the linear attenuation coefficient or radiodensity, of calcium is dependent on the X-ray spectrum and on characteristics of the CT detection system, and thus CT pixel or voxel values, e.g. calibrated in Hounsfield Units, of imaged volumes containing calcium, are dependent on properties of the radiation source and detector as well. Therefore, a calcium score may be considered as a semi-quantitative measure, that is inherently linked to the imaging system and modality used.

United States patent application US 2012/0076377 discloses a system and method for dual energy CT spectral imaging that provides for blood vessel stenosis visualisation and quantification. A data acquisition system is programmed to obtain a first set of CT image data for a region of interest at a first chromatic energy level, and to obtain a second set of CT image data for the region of interest at a second chromatic energy level. Plaque material is identified in the region of interest by analysing the second set of CT image data.

SUMMARY OF THE INVENTION

It is an object of embodiments of the present invention to provide good, efficient and/or robust methods and means for determining, e.g. calculating and/or estimating, a calcium content from CT data.

The above objective is accomplished by a method and device according to the present invention.

It is an advantage of embodiments of the present invention that coronary artery calcification can be quantified based on a CT image acquired by a low-dose CT scan protocol. It is an advantage of embodiments of the present invention that coronary artery calcification can be quantified based on a CT image acquired by a CT scan protocol that does not require a contrast agent to be injected in the patient. It is a further advantage of embodiments of the present invention that such quantification based on a low-dose and/or unenhanced CT scan protocol may be particularly suitable for medical screening applications.

It is an advantage of embodiments of the present invention that a robust and and/or motion-insensitive method, and corresponding means, is provided to calculate a quantitative calcium content.

It is an advantage of a method in accordance with embodiments of the present invention that it can be performed retrospectively, e.g. on a standard cardiac spectral CT scan, e.g. without requiring a dedicated imaging protocol specifically adapted for calcium scoring.

It is a further advantage of embodiments of the present invention that quantitative calcium scores can be obtained from images that were acquired in a volumetric CT imaging protocol, e.g. comprising multiple axial scans or a helical scan, that does not require electrocardiogram triggering or retrospective gating techniques to correct, compensate, prevent or reduce motion artefacts.

It is a further advantage of embodiments of the present invention that quantitative calcium scores can be obtained that are robust against, e.g. do not suffer a substantial deterioration of information quality due to, image blurring, such as blurring caused by residual breathing and/or cardiac motion.

It is an advantage of embodiments of the present invention that, while the observed attenuation of calcium, as represented by calibrated CT voxel values, e.g. in Hounsfield Units, depends on the x-ray spectrum and detector characteristics of the CT scanning system used to acquire the images, a calcium content determined by a device or method in accordance with embodiments of the present invention can be insensitive to such differences, e.g. can provide a reproducible and fully quantitative measurement of calcium content.

In a first aspect, the present invention relates to an image data processing device for determining a calcium content, e.g. for determining a calcium score, by analyzing cardiac spectral CT data. The image data processing device comprises a data input for receiving spectral CT projection data obtained by scanning a cardiac region of a subject using a spectral CT scanning unit, a modelling unit for applying a material decomposition algorithm to the spectral CT projection data such as to provide a calcium-specific component of the spectral CT projection data, a tomographic reconstruction unit for reconstructing the spectral CT projection data such as to provide a first 3D image of the cardiac region and for reconstructing the calcium-specific component of the spectral CT projection data such as to provide a second 3D image representative of calcium content in the cardiac region.

The device further comprises a segmentation unit for segmenting the first 3D image such as to provide an image mask corresponding to a cardiovascular structure of interest in the cardiac region, a selection unit for selecting a part of the second 3D image based on the image mask, and a computation unit for calculating a calcium content in the cardiovascular structure of interest based on the selected part of the second 3D image.

In an image data processing device in accordance with embodiments of the present invention, the segmentation unit may be adapted for providing the image mask corresponding to a coronary artery or part thereof in said cardiac region.

In an image data processing device in accordance with embodiments of the present invention, the selection unit may be adapted for selecting a first set of voxels of the second 3D image that form the cardiovascular structure of interest, e.g. the coronary artery or part thereof. In such device, the computation unit may be adapted for integrating an amount of calcium represented by the selected voxels such as to calculate the calcium content in the cardiovascular structure of interest.

In an image data processing device in accordance with embodiments of the present invention, the selection unit may be adapted for selecting a second set of voxels of the second 3D image that is the set complement of the voxels that form the cardiovascular structure of interest, e.g. the set complement of the first set of voxels.

An image data processing device in accordance with embodiments of the present invention may further comprise a forward projection unit for projecting the second set of voxels to generate simulated projection data corresponding to the same projections as the spectral CT projection data. The computation unit may furthermore be adapted for subtracting the simulated projection data from the calcium-specific component of the spectral CT projection data such as to obtain subtracted projection data representative of calcium specific attenuation in specifically the cardiovascular structure of interest.

In an image data processing device in accordance with embodiments of the present invention, the computation unit may be adapted for integrating an amount of calcium represented by each projection image comprised in the subtracted projection data to calculate a plurality of calcium content measurements.

In an image data processing device in accordance with embodiments of the present invention, the computation unit may be adapted for re-binning the subtracted projection data into projection images corresponding to parallel geometries prior to the integrating of the amount of calcium represented by each projection image.

In an image data processing device in accordance with embodiments of the present invention, the computation unit may be adapted for calculating a measure of statistical central tendency of the plurality of calcium content measurements.

In an image data processing device in accordance with embodiments of the present invention, the computation unit may be adapted for calculating a measure of statistical dispersion and/or a statistical confidence interval of the plurality of calcium content measurements.

In an image data processing device in accordance with embodiments of the present invention, the modelling unit may be adapted for partitioning the spectral CT projection data into the calcium-specific component and at least a first further component indicative of attenuation specific to soft tissue and/or water.

In an image data processing device in accordance with embodiments of the present invention, the modelling unit may be adapted for partitioning the spectral CT projection data into the calcium-specific component, the first further component and at least a second further component indicative of attenuation specific to a predetermined contrast agent.

In an image data processing device in accordance with embodiments of the present invention, the modelling unit may be adapted for implementing a forward model for detected photon counts represented by the spectral CT projection data, and for applying a maximum likelihood estimation method to determine a material length along each projection path for each modelled material, the modelled materials comprising at least calcium.

In a second aspect, the present invention also relates to a workstation comprising an image data processing device in accordance with embodiments of the first aspect of the present invention.

In a third aspect, the present invention also relates to an imaging system comprising an image data processing device in accordance with embodiments of the first aspect of the present invention and a spectral CT scanning unit for generating the spectral CT projection data when scanning the cardiac region and for supplying this spectral CT projection data to the data input.

In an imaging system in accordance with embodiments of the present invention, the spectral CT scanning unit may comprise an energy-resolving photon counting image detector.

In a fourth aspect, the present invention also relates to a method for determining a calcium content by analyzing cardiac spectral CT data. The method comprises obtaining spectral CT projection data corresponding to a scanned cardiac region of a subject, applying a material decomposition algorithm to the spectral CT projection data such as to provide a calcium-specific component of the spectral CT projection data, reconstructing the spectral CT projection data such as to provide a first 3D image of the cardiac region, reconstructing the calcium-specific component of the spectral CT projection data such as to provide a second 3D image representative of calcium content in the cardiac region, segmenting the first 3D image such as to provide an image mask corresponding to a cardiovascular structure of interest in the cardiac region, selecting a part of the second 3D image based on the image mask, and calculating a calcium content in the cardiovascular structure of interest based on the selected part of the second 3D image.

In a fifth aspect, the present invention also relates to a computer program product, having computer readable program code embodied therein, for calculating, when executed by a computer, a calcium content by analyzing cardiac spectral CT data, the calculation comprising performing the steps of a method in accordance with embodiments of the present invention.

Particular and preferred aspects of the invention are set out in the accompanying independent and dependent claims. Features from the dependent claims may be combined with features of the independent claims and with features of other dependent claims as appropriate and not merely as explicitly set out in the claims.

These and other aspects of the invention will be apparent from and elucidated with reference to the embodiment(s) described hereinafter.

Figure 1:
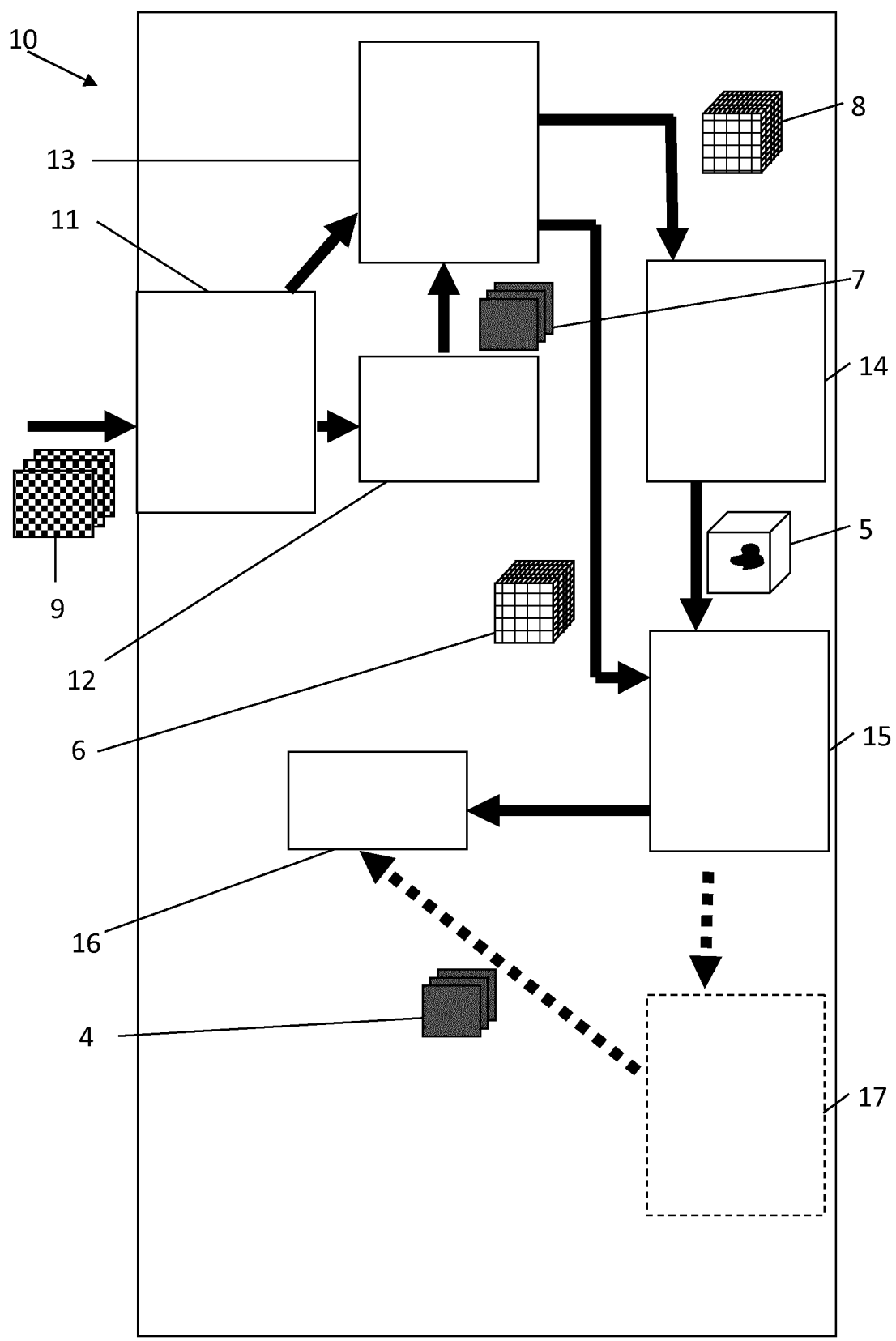
FIG. 1 illustrates, schematically, a device in accordance with embodiments of the present invention.

The drawings are only schematic and are non-limiting. In the drawings, the size of some of the elements may be exaggerated and not drawn on scale for illustrative purposes.

Any reference signs in the claims shall not be construed as limiting the scope.

In the different drawings, the same reference signs refer to the same or analogous elements.

DETAILED DESCRIPTION OF ILLUSTRATIVE EMBODIMENTS

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes. The dimensions and the relative dimensions do not correspond to actual reductions to practice of the invention.

Furthermore, the terms first, second and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments of the invention described herein are capable of operation in other sequences than described or illustrated herein.

Moreover, the terms top, under and the like in the description and the claims are used for descriptive purposes and not necessarily for describing relative positions. It is to be understood that the terms so used are interchangeable under appropriate circumstances and that the embodiments of the invention described herein are capable of operation in other orientations than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly it should be appreciated that in the description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

In the description provided herein, numerous specific details are set forth. However, it is understood that embodiments of the invention may be practiced without these specific details. In other instances, well-known methods, structures and techniques have not been shown in detail in order not to obscure an understanding of this description.

In a first aspect, the present invention relates to an image data processing device. This image data processing device may be suitable for generating medical relevant information in the form of a quantitative calcium measurement from diagnostic images.

FIG. 1 shows an exemplary image data processing device 10 in accordance with embodiments of the present invention. The data processing device 10 is adapted for determining a calcium content, e.g. for estimating and/or quantifying an amount of calcium, such as a mass or a volume of calcium, for example by measuring the amount of calcium or determining a value representative of such amount of calcium, e.g. for determining a calcium score.

The data processing device 10 is adapted for determining the calcium content by analyzing cardiac spectral computed tomography (CT) data, e.g. by analyzing raw data, e.g. particularly projection data such as projection images, acquired by a spectral CT scanning unit, e.g. a spectral CT scanner, e.g. a spectral photon counting CT scanning unit. For example, a data processing device 10 in accordance with embodiments of the present invention may be used to identify calcium using spectral CT imaging, e.g. spectral photon counting CT imaging. It is an advantage of embodiments of the present invention that a full quantitative measure can be obtained of calcium, e.g. a calcium score value can be determined that is directly and unambiguously linked to a physical quantity of calcium present in the scanned cardiac region. It is another advantage that a robust and motion-insensitive calcium score value can be determined, based on spectral decomposition, e.g. in the projection domain. It is yet another advantage that the data processing device 10 in accordance with embodiments of the present invention can be used for analysing projection data acquired by any cardiac spectral CT scan, e.g. without requiring a specific cardiac imaging protocol. It is another advantage that the data processing device 10 can be used for retrospective analysis, e.g. can determine an amount of calcium present in a cardiac spectral CT scan, where this cardiac spectral CT scan was not necessarily performed with the intention to determine such amount of calcium from the acquired images. In other words, an additional dedicated CT scan, specifically for allowing an amount of calcium to be determined, may not be required when using a device in accordance with embodiments of the present invention in routine cardiac spectral CT examination.

Particularly, the data processing device 10 may be adapted for determining a calcium content by analyzing cardiac spectral computed tomography (CT) data, acquired by a spectral CT scanning unit while executing a cardiac spectral CT imaging protocol that does not, necessarily, require breath holding, electrocardiogram (ECG) triggering or gating techniques to compensate for respiratory or cardiac motion.

The image data processing device 10 comprises a data input 11, e.g. comprising an input means such as a data communication network connection, a data carrier reader, or a dedicated device link, such as a data bus connection, connecting the image data processing device to a suitable data source, e.g. to a spectral CT scanning unit. The data input 11 is adapted for receiving spectral CT projection data 9 obtained by scanning a cardiac region of a subject, e.g. a patient, using a spectral CT scanning unit. Particularly, the projection data may be previously acquired by such scanning unit and transmitted, e.g. via a network or data bus connection or via a physical data carrier, to the data input for processing by the image data processing device 10.

The data input 11 may be adapted for receiving spectral CT projection data 9 corresponding to an unenhanced, low-dose, cardiac spectral CT scan, e.g. an unenhanced, low-dose, cardiac spectral photon counting CT scan. Hence, the image data processing device and its components may be adapted for processing such unenhanced, low-dose data. An unenhanced, low-dose CT scan may be routinely performed in patients undergoing cardiac CT, such that a device in accordance with embodiments can use such routinely available data to determine a robust and accurate measure of calcium content.

The data input 11 may be adapted for receiving spectral CT projection data 9 corresponding to a non-gated and/or non-motion-corrected cardiac spectral CT scan, e.g. a cardiac spectral photon counting CT scan that was acquired without usage of electrocardiogram (ECG) triggering, retrospective gating, or similar motion compensation techniques. Hence, the image data processing device and its components may be adapted for processing such non-gated and/or non-motion-corrected data. It is an advantage of a device in accordance with embodiments that, by not requiring motion compensation, suitable data to be processed may be more readily available, and, when acquiring data to be analysed, a lower radiation dose and/or faster scanning time may be achieved, as compared to images acquired while using conventional motion compensation techniques.

The data input 11 may be adapted for receiving spectral CT projection data 9 corresponding to a cardiac spectral CT scan that was acquired while not requiring a breath-hold of the subject. Hence, the image data processing device and its components may be adapted for processing such data. It is an advantage of a device in accordance with embodiments that, by not requiring breath holding during image acquisition, the comfort of the scanned subject may increase, and/or failed imaging runs due to involuntary or voluntary non-compliance with such breath-holding requirement can be prevented.

For example, a device 10 in accordance with embodiments of the present invention may be adapted, e.g. may serve to purpose, to provide calcium scoring for estimating the extent of coronary artery calcification. Such scoring may allow an operator to determine an early risk stratification, as patients with a high score may have an increased risk for a major adverse cardiac event.

While residual breathing and/or cardiac motion may deteriorate calcium scores determined by a conventional method known in the art, a device in accordance with embodiments of the present invention may be particularly robust for such motion artefacts, e.g. may produce accurate and reproducible calcium scores even when substantial motion blurring is present in the processed images.

The image data processing device 10 further comprises a modelling unit 12 for applying a material decomposition algorithm to the spectral CT projection data 9, e.g. for algorithmically decomposing the spectral CT projection data into components corresponding to contributions of different and/or specific materials to the information content of the spectral CT projection data.

The modelling unit 12 is adapted for applying this material decomposition algorithm such as to provide a calcium-specific component 7, indicative of calcium attenuation, of the spectral CT projection data 9, for example such as to provide a calcium-specific component indicative of a contribution to the information content of the spectral CT projection data that is specifically due to the presence and spatial distribution of calcium in the cardiac region that was scanned to obtain the spectral CT projection data.

For example, the modelling unit 12 may be adapted for partitioning the spectral CT projection data into this calcium-specific component and at least a first further component indicative of attenuation specific to soft tissue and/or water. For example, the projection images, acquired by a spectral CT detector, may be decomposed into calcium and water basis projections.

Thus, the projection images, acquired from a spectral CT detector, may be decomposed into calcium and water basis projections. However, more basis functions can be included, insofar the spectral separation, e.g. the spectral resolution, in the projection images provided by the detector allow for a more detailed decomposition.

For example, the modelling unit 12 may also be adapted for partitioning the spectral CT projection data into the calcium-specific component, the first further component and at least a second further component indicative of attenuation specific to a predetermined contrast agent. Thus, the image data processing device 10 may be adapted for receiving projection images as input that correspond to a contrast-enhanced cardiac spectral CT scan protocol. Advantageously, the contribution in the projection images due to a contrast agent can be accounted for efficiently by including the at least one second further component in the analysis, e.g. such as not to bias the calcium-specific component with the contrast component.

The modelling unit 12 may thus be adapted for performing a material decomposition in the projection domain. For example, the modelling unit may implement a forward model for the detected photon counts, e.g. represented by the pixel values in projection images constituting the spectral CT projection data 9, and may apply a maximum likelihood estimation method for determining the material length for each modelled material, e.g. at least a length of calcium along each projection path, e.g. preferably a length of calcium and a length of at least one other material, e.g. water or soft tissue, that would correspond to a best fit, or at least a good fit insofar stopping criteria of an iterative, converging algorithm are concerned, for explaining the detected counts. Such forward model may take the physical aspects of the detection system and the attenuation properties of the imaged object, e.g. the subject, into account. For example, the modelling unit may be adapted for taking the X-ray spectrum emitted by an X-ray source when acquiring the data corresponding to the cardiac region of the subject into account, e.g. may be adapted for receiving parameters defining such X-ray spectrum as input and for including such input in the forward model. The modelling unit may be adapted for taking the spectral response of an X-ray detector that acquired the data corresponding to the cardiac region of the subject into account, e.g. may be adapted for receiving parameters defining such spectral response as input and for including such input in the forward model. For example, the spectral attenuation of the subject may be modelled by two or more basis functions, e.g. corresponding to water and calcium, e.g. representative of soft tissue and bone materials. For example, in such forward model, the attenuation $\mu$, as function of energy E and position vector $\vec{x}$, may be modelled using an equation of the form:

$$\mu(E, \vec{x}) = \sum_{\alpha=1}^{N} a_\alpha(\vec{x}) f_\alpha(E),$$

in which the position-dependent functions $a_\alpha$ represent local densities, and the energy-dependent functions $f_\alpha$ represent mass attenuation coefficients, of a material indexed by the index $\alpha$ out of a total number of modelled materials N. For example, the energy dependence of the linear attenuation coefficient of materials for typical energies used in diagnostic CT imaging, e.g. in the range of 15 to 150 keV, may be adequately approximated by a linear combination of photoelectric and Compton scattering cross sections.

For example, in such maximum likelihood estimation method, a likelihood function $$P(m_1, \ldots, m_N | \lambda_1(A_\alpha), \ldots, \lambda_N(A_\alpha)) = \prod_{i=1}^{N} \frac{[\lambda_i(A_\alpha)]^{m_i}}{m_i!} e^{-\lambda_i(A_\alpha)}$$

may be optimized as function of the parameters $A_\alpha$, expressing the likelihood as a probability of an arbitrary measurement result matching the observed measurement result, e.g. photon counts $m_1, \ldots, m_N$ for N different energy bins, given a composition of the object parameterized by the parameters $A_\alpha$, e.g. the material lengths. The likelihood function may correspond to a combination, e.g. a multiplication, of Poisson random probability density functions, e.g. assuming the energy bins are independently distributed in accordance with Poisson distribution functions, however embodiments of the present invention are not limited to such choices of probability model, and may for example, use approximations of the Poisson distribution, more complex probability models taking noise and/or other factors into account, and/or may comprise interaction terms or a joint probability model where an independent distribution assumption would not be deemed inappropriate.

For example, the parameters $A_\alpha$ may be representative of line integrals of material components of the attenuation, e.g. line integrals of local density coefficients $A_\alpha = \int a_\alpha(\vec{x}) ds$, where the linear attenuation may be decomposed into different basis materials, e.g. including calcium, using these coefficients, e.g.

$$\mu(E, \vec{x}) = \sum_{\alpha=1}^{N_{mat}} a_\alpha f_\alpha.$$

In this example, $f_\alpha$ represents a material-specific cross-section, e.g. comprising cross-sections of the photo-electric effect, the Compton effect and K-edge contributions of the material.

$\lambda_i(A_\alpha)$ represents, in this example, an inferred mean value for the measurement $m_i$ in accordance with the probability model taking the material parameter $A_\alpha$ into account. For example, $$\lambda_i(A_1, A_2, A_3) = \int_0^\infty S_i(E) \Phi(E) e^{-\Sigma_{\alpha=1}^3 f_\alpha(E) A_\alpha} D(E) dE, i = 1, \ldots, N,$$

where D(E) refers to a detector absorption efficiency as function of energy, and $S_i(E)$ to sensitivities for the different energy bins, e.g. rectangular profile functions, e.g. a shifted Heaviside function or linear combination of shifted Heaviside functions, with limits determined by the respective threshold energies for each bin. However, embodiments of the present invention are not necessarily limited to such exemplary model relating the expected values of the observables to the likelihood optimization parameters.

As is known in the art, the likelihood function may be optimized, for example, by minimizing the negative log likelihood function, for convenience and computational efficiency, e.g.

$$\mathcal{L}(m_1, \ldots, m_N | A_\alpha) = -\ln[P(m_1, \ldots, m_N | \lambda_1(A_\alpha), \ldots, \lambda_N(A_\alpha))]$$

$$= \sum_{i=1}^{N} [\lambda_i(A_\alpha) + \ln m_i! - m_i \ln \lambda_i(A_\alpha)]$$

$$\simeq \sum_{i=1}^{N} [\lambda_i(A_\alpha) - m_i \ln \lambda_i(A_\alpha)].$$

The image data processing device 10 also comprises a tomographic reconstruction unit 13 for reconstructing, e.g. using a tomographic reconstruction technique as known in the art, the spectral CT projection data 9 such as to provide a first 3D image 8 of the cardiac region. The tomographic reconstruction unit 13 is furthermore adapted for reconstructing the calcium-specific component 7 of the spectral CT projection data such as to provide a second 3D image 6 representative of calcium content in the cardiac region.

For example, a standard 3D reconstruction may be performed by the tomographic reconstruction unit 13, in which all spectral channels present in the spectral CT projection data 9 may be used. This standard 3D reconstruction to provide the first 3D image 8 of the cardiac region may, for example, be performed on all spectral channels of the spectral CT projection data 9 and may cover the whole field-of-view (FOV).

Similarly, a 3D reconstruction may be performed by the tomographic reconstruction unit 13, in which the calcium-specific component 7 of the spectral CT projection data 9 is used. This 3D reconstruction to provide the second 3D image 6 may, for example, be performed on the calcium-specific component of the spectral CT projection data 9 specifically, and may cover the whole field-of-view (FOV). Preferably, the first 3D image 8 and the second 3D image 6 may be reconstructed in a corresponding coordinate grid, e.g. such as to obtain a one-on-one correspondence of the voxel elements in both images. However, this may not be necessary, as appropriate coordinate transformations can be taken into account, as will be appreciated by the skilled person, without any inventive effort, in performing the further processing steps described hereinbelow.

The image data processing device 10 further comprises a segmentation unit 14 for segmenting the first 3D image 8 such as to provide an image mask 5 corresponding to a cardiovascular structure of interest in the cardiac region.

The segmentation unit 14 may be adapted for segmentation of the whole heart region and/or a specific region of interest (ROI), on the standard 3D volume represented by the first 3D image 8. Suitable segmentation algorithms may be implemented by the segmentation unit 14, as known in the art, to perform this segmentation. For example, such segmentation algorithms may comprise voxel value thresholding operations, morphological filtering, curve and/or surface fitting operations, finite or infinite impulse response filters, processing using Markov random fields, watershed segmentation operations and/or other such techniques known in the art. The segmentation unit may be adapted for semi-automatically, or, preferably, automatically segmenting the cardiovascular structure of interest.

The cardiovascular structure may be a coronary artery or a part thereof. For example, the segmentation unit 14 may be adapted for providing an image mask 5 corresponding to a coronary artery or part thereof in the cardiac region.

The image data processing device 10 also comprises a selection unit 15 for selecting a part of the second 3D image 6 based on the image mask 5.

In an image data processing device 10 in accordance with embodiments of the present invention, the selection unit 15 may be adapted for selecting a first set of voxels of the second 3D image 6 that form the cardiovascular structure of interest. Thus, the region of interest defined by the image mask may be used to mask out the corresponding voxels in the 3D calcium volume represented by the second 3D image 6.

In an image data processing device 10 in accordance with embodiments of the present invention, the selection unit 15 may be adapted for selecting a second set of voxels of the second 3D image 6, e.g. alternatively or additionally to the selection of the first set of voxels referred to hereinabove. In such embodiments, this second set of voxels is the set complement of the voxels that form the cardiovascular structure of interest, e.g. the second set of voxels is the set complement of the first set of voxels. This second set of voxels being a 'set complement' of the first set of voxels refers to the set-theoretic concept of a set of voxels formed by all voxels of the second 3D image 6 that are not included in the first set.

The image data processing device 10 also comprises a computation unit 16 for calculating a calcium content in the cardiovascular structure of interest based on the selected part of the second 3D image 6.

In an image data processing device 10 in accordance with embodiments of the present invention, the computation unit 16 may be adapted for integrating an amount of calcium represented by selected voxels, e.g. the first set of voxels referred to hereinabove, such as to calculate the calcium content in the cardiovascular structure of interest.

The computation unit 16 may be adapted for outputting at least one value indicative of the calculated calcium content, e.g. a calcium score. For example, the image data processing device 10 may comprise a display device, such as a display monitor, a printer, a digital data carrier writer, e.g. a port for interfacing with a portable memory or data disk device and/or an optical disc writer, and/or a data network interface for respectively displaying, printing, writing and/or transmitting the at least one value indicative of the calculated calcium content.

Furthermore, the image data processing device 10 may comprise a forward projection unit 17 for projecting the second set of voxels, referred to hereinabove, to generate simulated projection data 4 corresponding to the same projections as the spectral CT projection data 9. This simulated projection data may thus contain projections, e.g. projection images, of the calcium not included in the cardiovascular structure of interest, e.g. calcium in ribs and/or vertebrae that were present in the field-of-view when imaging the cardiac region.

In accordance with embodiments of the present invention, the computation unit 16 may be adapted for subtracting the simulated projection data 4 from the calcium-specific component 7 of the spectral CT projection data to obtain subtracted projection data representative of calcium specific attenuation in specifically the cardiovascular structure of interest.

The computation unit 16 may be adapted for integrating an amount of calcium represented by each projection image comprised in the subtracted projection data to calculate a plurality of calcium content measurements. Since the projected amount of calcium in each projection view may be substantially constant, a robust measure can be obtained from the multiple redundant measurements.

The computation unit 16 may be adapted for determining a plurality of parallel projection images from the subtracted projection data, e.g. by re-binning the subtracted projection data into projections corresponding to parallel geometries. The computation unit 16 may be adapted for integrating an amount of calcium represented by each of the parallel projection images to calculate a plurality of calcium content measurements.

Thus, the computation unit 16 may be adapted for re-binning the subtracted projection data into projection images corresponding to parallel geometries prior to this integrating of the amount of calcium represented by each projection image, e.g. by each re-binned projection image.

The computation unit 16 may be adapted for calculating a measure of statistical central tendency of the plurality of calcium content measurements. For example, such measure of statistical central tendency may comprise a mean, a median, a modal value, an arithmetic mean, a geometric mean, a weighted mean, and/or a similar measure for statistically summarizing a central tendency of a plurality of comparable values known in the art.

The computation unit 16 may also be adapted for calculating a measure of statistical dispersion and/or a statistical confidence interval of the plurality of calcium content measurements. For example, such measure of statistical dispersion may comprise an interquartile range, a variance, a standard deviation, or a similar measure for statistically summarizing a dispersion of a plurality of comparable values known in the art.

In another aspect, the present invention also relates to a workstation comprising an image data processing device in accordance with embodiments of the first aspect of the present invention. For example, such workstation may comprise a computer, e.g. which may serve as an operator console. The workstation may comprise a human readable output device such as a monitor or display and a human interface input device such as a keyboard and mouse. The operator may interact with the image data processing device in a non-interactive or interactive manner, e.g. using a graphical user interface or otherwise. The workstation may be adapted for controlling a CT scanning unit operably connected to the data input 11. However, a workstation in accordance with embodiments is not necessarily operably connected to such CT scanning unit. For example, projection data may be acquired substantially independent from the processing of such data by operating the workstation.

Figure 2:
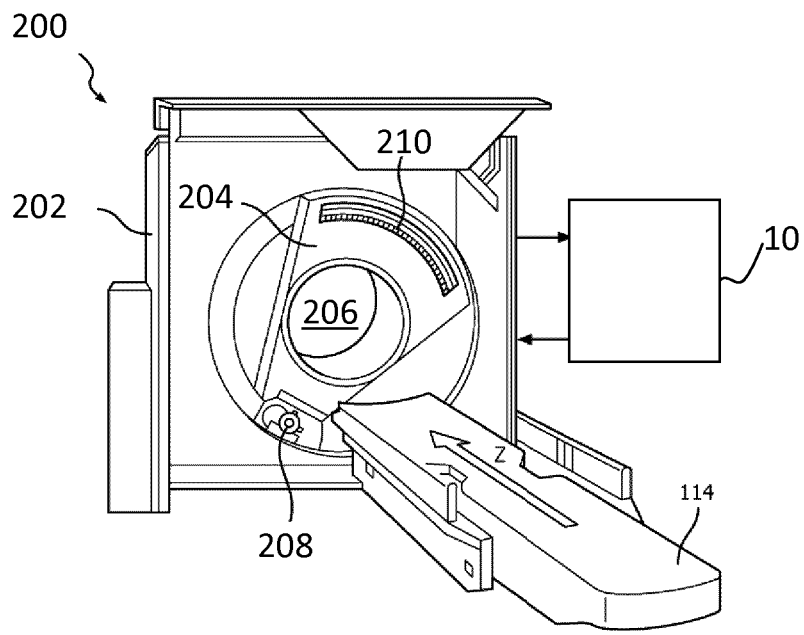
FIG. 2 illustrates, schematically, an imaging system in accordance with embodiments of the present invention.

In another aspect, the present invention also relates to an imaging system comprising an image data processing device in accordance with embodiments of the first aspect of the present invention, and a spectral CT scanning unit for generating the spectral CT projection data 9 when scanning the cardiac region. The spectral CT scanning unit is also adapted for supplying the spectral CT projection data 9 to the data input 11. For example, FIG. 2 illustrates an exemplary imaging system 200 in accordance with embodiments of the present invention.

In an imaging system in accordance with embodiments of the present invention, the spectral CT scanning unit may be adapted for performing multiple axial scans and/or a helical scan of the cardiac region such as to generate the spectral CT projection data 9.

In an imaging system in accordance with embodiments of the present invention, the spectral CT scanning unit may comprise an energy-resolving photon counting image detector.

The spectral CT scanning unit may comprise a radiation source that emits radiation for traversing the cardiac region of the subject when acquiring the projection data.

For example, the spectral CT scanning unit, e.g. the computed tomography scanner, may comprise a stationary gantry 202 and a rotating gantry 204, which may be rotatably supported by the stationary gantry 202. The rotating gantry 204 may rotate, about a longitudinal axis, around an examination region 206 for containing the cardiac region of the subject when acquiring the projection data. The spectral CT scanning unit may comprise a subject support, such as a couch, to support the subject in the examination region 206.

The spectral CT scanning unit may comprise a radiation source 208, such as an x-ray tube, which may be supported by and configured to rotate with the rotating gantry 204. The radiation source may include an anode and a cathode. A source voltage applied across the anode and the cathode may accelerate electrons from the cathode to the anode. The electron flow may provide a current flow from the cathode to the anode, such as to produce radiation for traversing the examination region 206.

The spectral CT scanning unit may comprise a detector array 210. This detector array may subtend an angular arc opposite the examination region 206 relative to the radiation source 208. The detector array may include a one or two dimensional array of pixels, such as direct conversion detector pixels, which include a direct conversion material such as cadmium telluride (CdTe), cadmium zinc telluride (CZT), and/or other direct conversion material. The detector array may be adpated for detecting radiation traversing the examination region and for generating a signal indicative of an energy thereof.

Furthermore, the spectral CT scanning unit may comprise an energy discriminator, e.g. comprising a plurality of comparators configured for a corresponding plurality of energy thresholds, for evaluating the generated signal in view of its associated energy. The spectral CT scanning unit may comprise a counter, e.g. a plurality of counters, e.g. for incrementing count values for each energy threshold based on the output of the energy discriminator. The spectral CT scanning unit may comprise an energy binner for organizing the counts in a plurality of energy bins, each bin representing a different energy range.

In yet another aspect, the present invention relates to a method for determining a calcium content, e.g. for determining a coronary artery calcium score.

Figure 3:
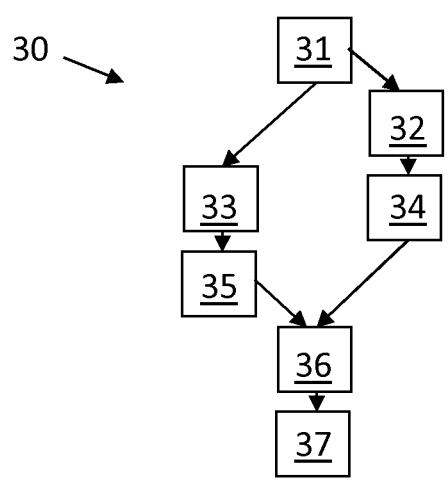
FIG. 3 illustrates, schematically, a method in accordance with embodiments of the present invention.

Referring to FIG. 3, an exemplary method 30 in accordance with embodiments of the present invention comprises a step of obtaining 31 spectral CT projection data 9 that corresponds to a scanned cardiac region of a subject. For example, the spectral CT projection data may be pre-generated by a spectral CT scanner, e.g. a photon counting spectral CT scanning unit.

The method 30 further comprises applying 32 a material decomposition algorithm to the spectral CT projection data 9 such as to provide a calcium-specific component 7 of the spectral CT projection data 9.

The method further comprises reconstructing 33 the spectral CT projection data 9 such as to provide a first 3D image 8 of the cardiac region.

The method also comprises reconstructing 34 the calcium-specific component 7 of the spectral CT projection data 9 such as to provide a second 3D image 6 representative of calcium content in the cardiac region.

The method 30 comprises a further step of segmenting 35 the first 3D image 8 such as to provide an image mask 5 corresponding to a cardiovascular structure of interest in the cardiac region, e.g. a heart, a part of the heart, a coronary artery, or a part thereof, such as a section of interest of a coronary artery.

The method further comprises selecting 36 a part of the second 3D image 6 based on the image mask 5.

The method also comprises calculating 37 a calcium content in the cardiovascular structure of interest based on the selected part of the second 3D image 6.

In a yet further aspect, the present invention also relates to a computer program product, having computer readable program code embodied therein, for calculating, when executed by a computer, a calcium content by analyzing cardiac spectral CT data. In such computer program product, the calculation comprises performing the steps of a method in accordance with embodiments of the present invention.

The invention claimed is:

1. An image data processing device for determining a calcium content by analyzing cardiac spectral CT data, the image data processing device comprising:
a memory that stores a plurality of instructions;
processor circuitry that couples to the memory and that is configured to execute the plurality of instructions to:
receive spectral CT projection data obtained by scanning a cardiac region of a subject using a spectral CT scanning unit;
apply a material decomposition algorithm to said spectral CT projection data such as to provide a calcium-specific component of said spectral CT projection data;
reconstruct said spectral CT projection data such as to provide a first 3D image of said cardiac region and for reconstructing said calcium-specific component of the spectral CT projection data such as to provide a second 3D image representative of calcium content in said cardiac region;
segment said first 3D image such as to provide an image mask corresponding to a cardiovascular structure of interest in said cardiac region, wherein both of the segmented first 3D image and the second 3D image are derived from the same spectral CT projection data;
select a part of said second 3D image based on said image mask; and
calculate a calcium content in said cardiovascular structure of interest based on said selected part of the second 3D image.

2. The image data processing device of claim 1, wherein the processor circuitry is further configured to provide the image mask corresponding to a coronary artery or part thereof in said cardiac region.

3. The image data processing device of claim 1, wherein the processor circuitry is further configured to select a first set of voxels of said second 3D image that form said cardiovascular structure of interest, and wherein the processor circuitry is further configured to integrate an amount of calcium represented by said selected voxels such as to calculate the calcium content in the cardiovascular structure of interest.

4. The image data processing device of claim 1, wherein the processor circuitry is further configured to select a second set of voxels of said second 3D image that is the set complement of the voxels that form said cardiovascular structure of interest, wherein the processor circuitry is further configured to project the second set of voxels to generate simulated projection data corresponding to the same projections as said spectral CT projection data, and wherein the processor circuitry is further configured to subtract said simulated projection data from said calcium-specific component of the spectral CT projection data to obtain subtracted projection data representative of calcium specific attenuation in specifically the cardiovascular structure of interest.

5. The image data processing device of claim 4, wherein the processor circuitry is further configured to integrate an amount of calcium represented by each projection image comprised in said subtracted projection data to calculate a plurality of calcium content measurements.

6. The image data processing device of claim 5, wherein the processor circuitry is further configured to re-bin said subtracted projection data into projection images corresponding to parallel geometries prior to said integrating of the amount of calcium represented by each projection image.

7. The image data processing device of claim 5, wherein the processor circuitry is further configured to calculate a measure of statistical central tendency of said plurality of calcium content measurements.

8. The image data processing device of claim 5, wherein the processor circuitry is further configured to calculate a measure of statistical dispersion and/or a statistical confidence interval of said plurality of calcium content measurements.

9. The image data processing device of claim 1, wherein the processor circuitry is further configured to partition the spectral CT projection data into said calcium-specific component and at least a first further component indicative of attenuation specific to soft tissue and/or water.

10. The image data processing device of claim 9, wherein the processor circuitry is further configured to partition the spectral CT projection data into said calcium-specific component, said first further component and at least a second further component indicative of attenuation specific to a predetermined contrast agent.

11. The image data processing device of claim 1, wherein the processor circuitry is further configured to implement a forward model for detected photon counts represented by said spectral CT projection data, and to apply a maximum likelihood estimation method to determine a material length along each projection path for each modelled material, the modelled materials comprising at least calcium.

12. A workstation comprising the image data processing device of claim 1.

13. An imaging system comprising the image data processing device of claim 1, and a spectral CT scanner generating said spectral CT projection data when scanning said cardiac region and supplying this spectral CT projection data to said data input.

14. A method for determining a calcium content by analyzing cardiac spectral CT data, the method comprising:
obtaining spectral CT projection data corresponding to a scanned cardiac region of a subject;
applying a material decomposition algorithm to said spectral CT projection data such as to provide a calcium-specific component of said spectral CT projection data;
reconstructing said spectral CT projection data such as to provide a first 3D image of said cardiac region;
reconstructing said calcium-specific component of the spectral CT projection data such as to provide a second 3D image representative of calcium content in said cardiac region;

segmenting said first 3D image such as to provide an image mask corresponding to a cardiovascular structure of interest in said cardiac region, wherein both of the segmented first 3D image and the second 3D image are derived from the same spectral CT projection data;

selecting a part of said second 3D image based on said image mask; and calculating a calcium content in said cardiovascular structure of interest based on said selected part of the second 3D image.

15. A non-transitory computer-readable medium having computer readable program code for calculating, when executed by a computer, a calcium content by analyzing cardiac spectral CT data, in which said calculation comprises performing a method for determining a calcium content by analyzing cardiac spectral CT data, the method comprising:

obtaining spectral CT projection data corresponding to a scanned cardiac region of a subject;

applying a material decomposition algorithm to said spectral CT projection data such as to provide a calcium-specific component of said spectral CT projection data;

reconstructing said spectral CT projection data such as to provide a first 3D image of said cardiac region;

reconstructing said calcium-specific component of the spectral CT projection data such as to provide a second 3D image representative of calcium content in said cardiac region;

segmenting said first 3D image such as to provide an image mask corresponding to a cardiovascular structure of interest in said cardiac region, wherein both of the segmented first 3D image and the second 3D image are derived from the same spectral CT projection data;

selecting a part of said second 3D image based on said image mask; and calculating a calcium content in said cardiovascular structure of interest based on said selected part of the second 3D image.

16. The image data processing device of claim 1, wherein the processor circuitry is further configured to generate simulated projection data corresponding to the same projections as said spectral CT projection data.

* * * * *